(12) United States Patent
Weinzweig

(10) Patent No.: US 11,911,082 B2
(45) Date of Patent: Feb. 27, 2024

(54) BONE FIXATION METHODS AND DEVICES INCLUDING ADHESIVE BIOACTIVE RESORBABLE BONE PLATES

(71) Applicant: NovaPlast Corporation, Summerland Key, FL (US)

(72) Inventor: Jeffrey Weinzweig, Highland Park, IL (US)

(73) Assignee: Novaplast Corporation, Summerland Key, FL (US)

( * ) Notice: Subject to any disclaimer, the term of this patent is extended or adjusted under 35 U.S.C. 154(b) by 260 days.

(21) Appl. No.: 16/725,658

(22) Filed: Dec. 23, 2019

(65) Prior Publication Data

US 2020/0146732 A1 May 14, 2020

Related U.S. Application Data

(63) Continuation of application No. 15/357,294, filed on Nov. 21, 2016, now Pat. No. 10,512,492, and a continuation of application No. 15/185,458, filed on Jun. 17, 2016, now abandoned, and a continuation of application No. 14/465,566, filed on Aug. 21, 2014, now Pat. No. 9,370,385.

(51) Int. Cl.
| | |
|---|---|
| *A61B 17/80* | (2006.01) |
| *A61B 17/00* | (2006.01) |
| *A61L 31/06* | (2006.01) |
| *A61L 31/14* | (2006.01) |
| *A61L 31/16* | (2006.01) |
| *C09J 167/04* | (2006.01) |

(52) U.S. Cl.
CPC ........ *A61B 17/80* (2013.01); *A61B 17/00491* (2013.01); *A61L 31/06* (2013.01); *A61L 31/146* (2013.01); *A61L 31/16* (2013.01); *C09J 167/04* (2013.01); *A61B 2017/00004* (2013.01); *A61B 2017/005* (2013.01); *A61L 2300/412* (2013.01); *A61L 2430/02* (2013.01)

(58) Field of Classification Search
CPC .................... A61B 17/8085; A61B 17/00491
See application file for complete search history.

(56) References Cited

U.S. PATENT DOCUMENTS

| | | | | |
|---|---|---|---|---|
| 2008/0234754 | A1* | 9/2008 | McCarthy | A61L 24/043 606/280 |
| 2016/0144067 | A1* | 5/2016 | Armbruster | A61F 2/30907 604/307 |

* cited by examiner

*Primary Examiner* — Olivia C Chang
(74) *Attorney, Agent, or Firm* — Joseph M. Kuo; Saul Ewing, LLP

(57) ABSTRACT

A bone fixation system, device and method are provided herein. A system may include a bone plate. The bone plate is adapted to be affixed to a bone surface, and comprises a bioactive porous portion. The porous portion is adapted to, include bone healing-promoting substances, such as hollow microparticles containing the bone healing-promoting substances embedded in the porous portion. The bone plate father includes at least one attachment portion. In some embodiments, the attachment portion includes a face, which defines indentations, such as dimples, to retain an amount of adhesive.

7 Claims, 21 Drawing Sheets

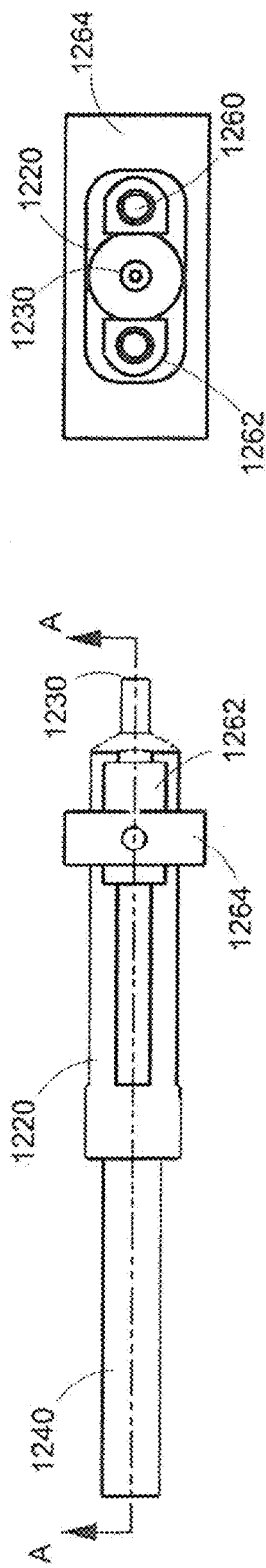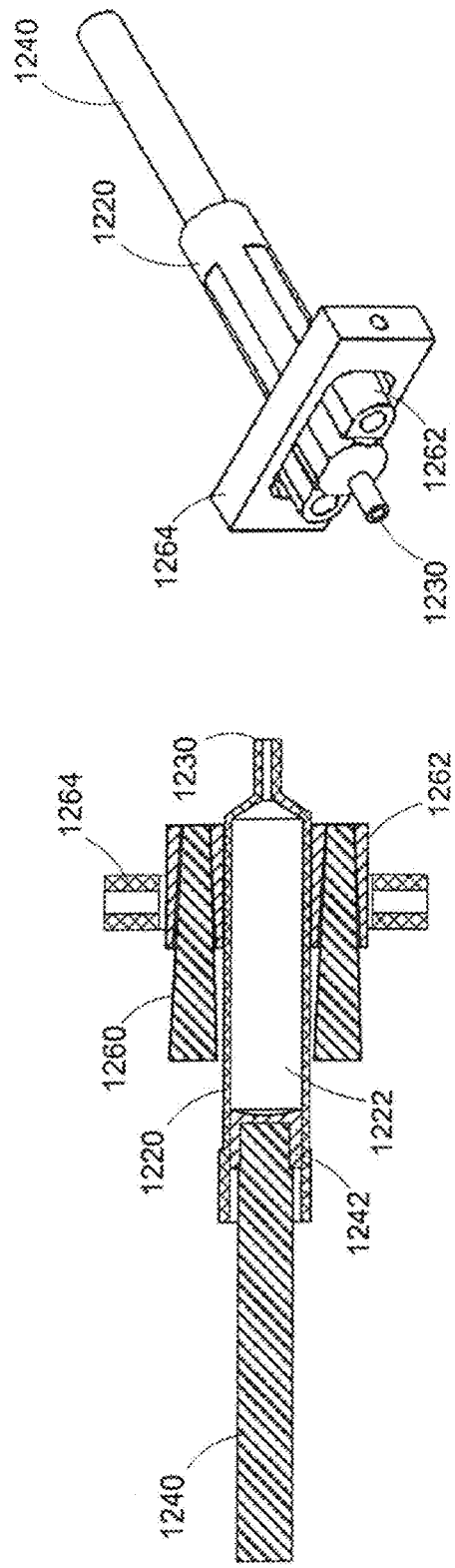

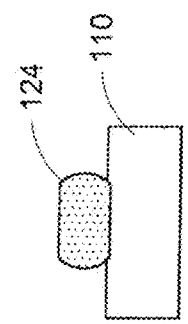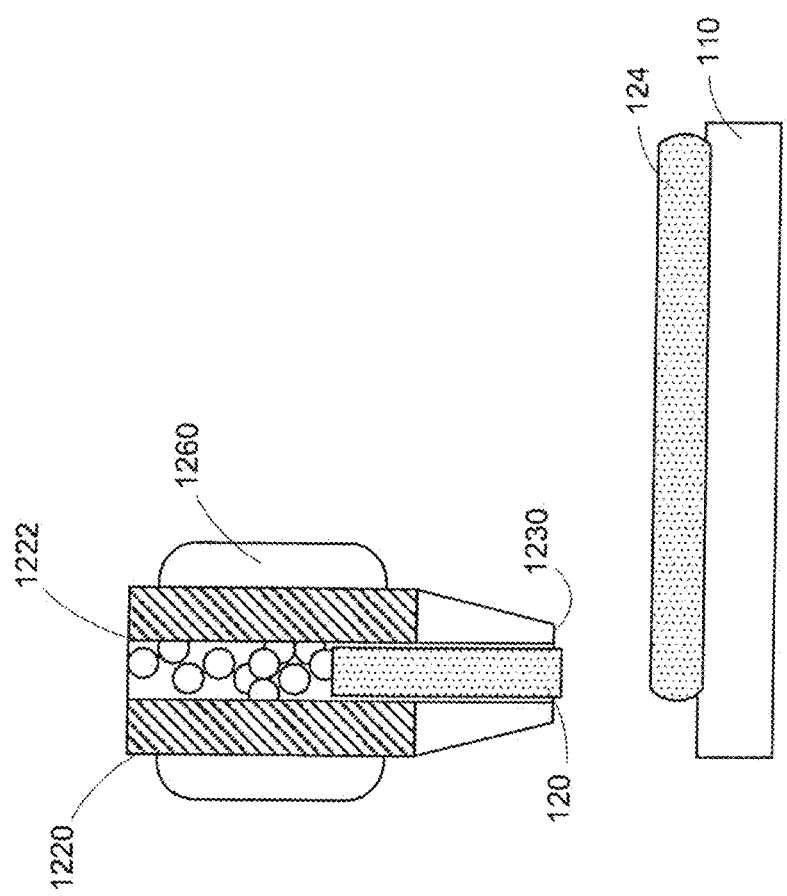
FIGURE 16B
FIGURE 16A

BONE FIXATION METHODS AND DEVICES INCLUDING ADHESIVE BIOACTIVE RESORBABLE BONE PLATES

PRIORITY OF THE INVENTION

This application is a continuation of U.S. patent application Ser. No. 15/357,294 filed on Nov. 21, 2016, and entitled "Bone Fixation Methods and Devices Including Adhesive Bioactive Resorbable Bone Plates," which is a continuation of U.S. patent application Ser. No. 15/185,458 filed on Jun. 17, 2016, and entitled "Bone Fixation Methods and Devices," which is a continuation of application Ser. No. 14/465,566 filed on Aug. 21, 2015 and was patented on Jun. 21, 2016 as U.S. Pat. No. 9,370,385. This application further claims priority to U.S. Provisional application Ser. No. 62/259,961 entitled "Adhesive Bioactive Resorbable Bone Plates." These references are incorporated herein by reference in their entireties.

BACKGROUND

Craniomaxillofacial surgery is performed routinely in the United States and around the world for numerous problems involving the skull, including craniosynostosis (premature fusion of the cranial sutures), skull deformities associated with syndromes such as Crouzon Syndrome and Apert Syndrome skull deformities resulting from the resection of both benign and malignant tumors, and complex craniofacial trauma involving the bones of the face and skull. These surgeries may involve the alteration or correction of the shape and structure of the skull, face and jaws and often require the repair, manipulation and fixation of bone.

Presently, the approximation and fixation of bone is typically accomplished with mechanical fastening systems, such as screws and plates. Tissue conditions, limited space, and access to the surgical site often present particular challenges to the practitioner. For example, it some cases, mechanical fixation is complicated or even, prevented altogether due to a tack of tissue surface area or tissue substrate depth sufficient to afford an adequate secure location for the fixation device. In addition, standard mechanical attachment methods in the context of bone repairs involve a series of labor intensive and sometimes complicated tasks.

At present, several types of craniofacial surgery plating systems are commercially available. Both titanium and resorbable polymer-based systems utilizing plates and screws are routinely utilized for the stabilization of bones during reconstruction in various craniomaxillofacial surgeries. These systems, however, often require cumbersome power equipment that necessitates additional operating room staff training and additional surgical time that increases the cost of the operating room, anesthesia time and surgical time. Sonic welding products, such as the Sonic Weld™ produced by KLS Martin, utilize a plate and resorbable tacks inserted into a hole drilled into the bone tissue and welded in place with an ultrasome welding device. While these products do not use conventional screws, holes cast still be drilled into the bone tissue for placement of the tacks, which melt and disseminate into the trabecula of the bone with unknown consequences on growth and, development.

The type, weight and amount of material used in plating present additional challenges. Internal fixation devices, such as those used in craniomaxillofacial surgery historically have been made of various materials including metals such as titanium. Polylactic acid or polylactide polymers, such as poly(L-lactic acid) (PLLA) and poly(lactic-co-glycolide) (PLEA)) have also been used in implantable devices. As compared to metallic devices, fixation devices made of these types of polymers do trot corrode, can be constructed to avoid stress yielding, and are resorbable. Further, these devices may be particularly useful in the pediatric patient population as their resorption eliminates any adverse or restrictive effect that permanent plates would impose on craniomaxillofacial growth and development. Resorption of plates and screws fabricated from these polymers occurs approximately 2 years following placement. While use of biodegradable and absorbable materials is, preferred by the surgical community, many of the existing mechanical systems are fabricated from metal and are non-resorbable. Conventional plating systems utilizing screws can often weaken the underlying bone or tissue, leading to decreased trabecular bone score. In some cases, failure of the screws can occur. Further, the thickness of these devices necessary to support screws, and the screws themselves, may be uncomfortable for the patient, be visible from the outer tissue surface, or interfere with healing.

Although some tools and materials have been developed to overcome the challenges and shortcomings described above, the fixation devices are still often bulky and cumbersome and time consuming to implant. A need still exists for a method and device that can eliminate the need for screws, but still provide satisfactory bony stabilization for craniofacial reconstruction and other reconstructive or orthopedic surgeries by (1) simplifying and expediting the intra-operative application of plates to the bone, and (2) removing the need for drilling holes in the bone tissue, thereby obviating the need for bulky power drilling equipment. Such a method, and device would eliminate many of the surgical steps required to place mechanical fixation devices. In particular, drilling, tapping to produce threading, and placement of fixation pins or screws would no longer be necessary. Further, a device which utilizes a biocompatible, absorbable and lightweight polymer material may also address many of the above issues. It may also be useful to provide an internal fixation system that contributes to the quality of bone healing by the administration of growth factors or other biologically-active (bioactive) molecules.

In earlier work, the inventor developed novel systems and methods for repairing bone defects using an applicator device for dispensing a melted adhesive either directly on the bone tissue as the fixation means, or in combination with a bone plate. In other work, systems and methods for adhering a bone plate to a bone surface by way of an adhesive and without the use of mechanical fixation means were developed in whole or in part by the inventor. In still other works, the inventor developed systems and methods whereby adhesive in a melted state is applied to a first bone segment and a second bone segment in abutment with the first bone segment, and the adhesive is cured so as to affix the first bone segment to the second bone segment. These advancements are disclosed in U.S. Pat. No. 9,370,385 entitled Bone Fixation Methods and Devices; U.S. Pat. No. 9,173,970 entitled, Biodegradable Bone Plates and Bonding Systems; and U.S. Pat. No. 8,870,871 entitled, Biodegradable Bone Plates and Bonding Systems, the disclosures of which are incorporated herein by reference.

During craniomaxillofacial surgery surgeons also encounter adverse conditions that inhibit or prevent adequate bony healing. As a result, fibrous union, non-union, and delayed bony healing may be produced. This contributes to the formation of osteomyelitis, osteoradionecrosis, bone destruction and bone loss. Such adverse conditions may include patient exposure to radiation, infection, and chemotherapeutic agents. As a result, multiple subsequent procedures are often necessary to debride infected and necrotic bone and reconstruct lost bone with bone grafts. Amelioration of the detrimental effects of these conditions on bony healing would reduce the incidence of bony complications and mitigate the need for subsequent procedures while expediting patient recovery.

For example, studies over the past, decade have demonstrated the efficacy of growth factors, antibiotics, and supplemental vitamins in the promotion of soft tissue and bony healing in various impaired models. These studies demonstrate that the advantage of providing such substances directly to the site of healing—i.e., the bony osteotomy—is significant.

SUMMARY OF THE INVENTION

Novel systems and methods for repairing bone defects using an applicator device for dispensing a melted adhesive either directly on the bone tissue as the fixation meals, or in combination with a bone plate, are described herein. The adhesive can be any heat-meltable, bioabsorbable material. In some cases, the adhesive is provided as or includes a polymer material, such as polylactic acid) ("PLA") or a PLA-based polymer such as poly-DL-lactide (PDLLA). Many sizes and shapes of plates may also be provided and selected by a surgeon based on his or her preference or to meet a particular surgical need. For example, plates may be arc or cross-shaped, or may be cut-to-size from a sheet, or spool of plate material. The applicator device is configured to melt and dispense the adhesive in a controlled manner. In some embodiments, the applicator device may include a control mechanism for dispensing precise amounts of adhesive and ensuring that excess adhesive is not dispensed onto the bone or plate. The device may be provided in the form a surgical tool that can be operated with one hand, leaving a free band for the surgeon to manipulate the tissue or plate.

Some embodiments of the present, disclosure provide a system including; (i) a plate having at least one face configured to be affixed to a bone surface; and (ii) an adhesive for affixing the plate to a bone surface.

Further embodiments of the present disclosure provide a method including: (i) applying an adhesive in a melted state to a first bone segment and a second bone segment in abutment with the first bone segment; and (ii) curing the adhesive thereby affixing the first bone segment to the second bone segment.

Further embodiments of the present disclosure provide a method including; (i) applying a bioabsorbable polymer adhesive in a melted state to a plate configured to be affixed to a bone; (ii) bringing the plate into contact with a first bone segment and a second bone segment in abutment with the first bone; and (iii) curing the adhesive thereby affixing the plate to the first bone segment and to the second bone segment.

Still further embodiments of the present disclosure provide a fixation device, including a plate having at least one face configured to be affixed to a bone surface, the at least one thee having a plurality of indentations or "dimples" for receiving an amount, of adhesive.

Still other aspects of the present invention relate to systems and methods for promoting bone healing. In some embodiments of the present invention, the system and method includes the introduction of bone healing-promoting substances, such as growth factors, antibiotics, and supplemental vitamins, directly to the site where bony healing is occurring. For example, the bone healing-promoting substances are introduced at the fracture site or the osteotomy site. The present invention comprises a resorbable, biodegradable bone plate that includes a porous section. This porous section is then Impregnated with the bone healing-promoting substances. In a preferred embodiment, hollow microparticles, such as nanospheres and microspheres containing the desired substances, e.g., growth factors, antibiotics, supplemental vitamins, etc., are embedded within the porous section.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 13A is a side view of a component of an example application device for use in the system of FIG. 1.

FIG. 13B is a front view of a component of an example application device for use in the system of FIG. 1.

FIG. 13C is a side cross-sectional view taken along line A-A of a component of an example application device for use in the system of FIG. 1.

FIG. 13D is a perspective view of a component of an, example application device for use in the system of FIG. 1.

FIG. 16A is a side partial cross-sectional view of a portion of an, example application device for use in the system of FIG. 1, shown applying a ribbon of adhesive to a fixation device.

FIG. 168 is a front view of a ribbon of adhesive applied to a fixation device.

DETAILED DESCRIPTION OF PREFERRED EMBODIMENTS OF THE INVENTION

Figure 1:
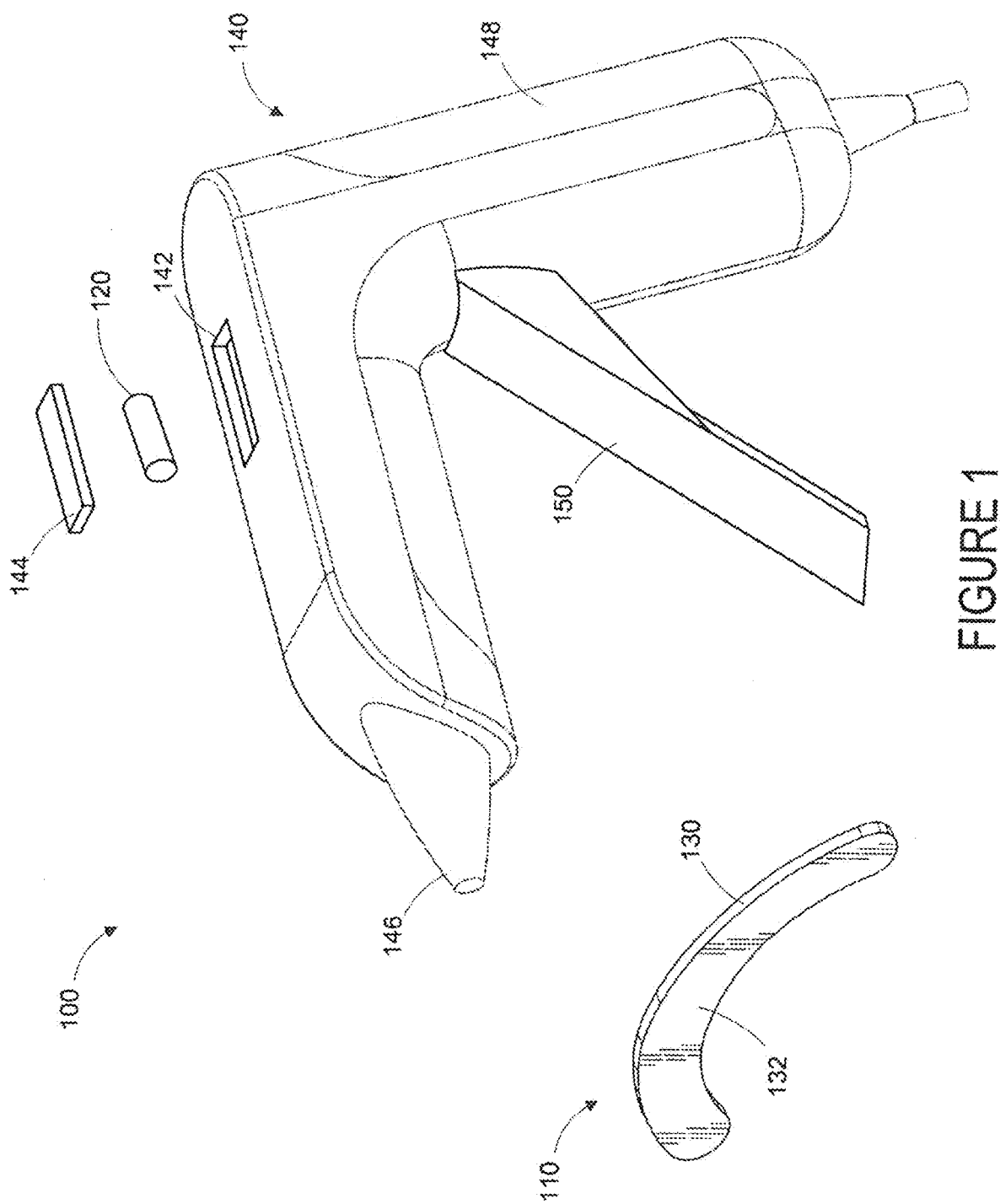
FIG. 1 is a view of an example system.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Novel systems, devices and, methods for repairing bone defects are described herein. Example methods may include dispensing an adhesive directly on a bone surface as the fixation means, or using the adhesive to affix a fixation device, such as a bone plate, to the surface of one or more bone segments. The plate is affixed, in one example, by applying the adhesive in a melted state and holding the plate in place while it cures or hardens. Where the adhesive alone is used to affix hone segments together or till in a void, the adhesive material is applied to each of the bone segments. Both example methods can be utilized in a number of geometrically varied bone shapes.

The described systems and methods may overcome many of the shortcoming's described above by eliminating the need for screws, pins or other implements which must be physically driven into the bone tissue and also by eliminating the need for the secondary operation of drilling holes to receive these fastening implements in the bone. This may not only reduce the potential for damage to bony segments, but may also maintain the resorption characteristics of the bone plate. Moreover, the need for bulky and expensive hone drills for affixing the bone plates and the time associated with drilling holes in the bone is also eliminated.

Eliminating the use of screws and pins also provides considerable flexibility in the size and shape of the bone plates. The thickness of the plates may also be reduced while still maintaining superior tensile and mechanical properties such as stiffness, toughness, and elongation to break. In some cases, the bone plates may include one or more indentations, such as dimples or grooves, for receiving the adhesive, which may include any biocompatible and absorbable adhesive. These indentations provide a convenient guide for dispensing precise amounts of the adhesive to the plates and, in some cases, in defined patterns. Further, the bone plates may provide a vessel for controlled delivery of one or more medicinal agents to the surgical site. In some embodiments, the plate may include one or more bioactive portions, which may be porous, and that is impregnated with one or more medicinal agents. The term "medicinal agent" as used herein should be understood broadly to include any substances having any biologic, pharmacological, remedial, prophylactic, analgesic, therapeutic, preventative, or curative properties. Such bioactive portions of the bone plate with bone-healing promoting substances will reduce recovery time for the patient.

Adhesive may be applied to the bone surface or bone plates using a novel application device. The system may also include a novel application device for heating and dispensing the adhesive onto a fixation device or onto the bone surface. In one example, the application device is in the form of a hand held surgical tool that can process the heating of the adhesive material and then deliver the material to the surgical site. The device used for delivery of the materials includes a novel control mechanism and features to implement an effective bone repair. The device may be manipulated and adhesive dispensed with a single hand so that the operator may have a free hand to position the bone plate or bone segments. Further, operation of the device may be simple such that it may be readily used, not only by surgeons, but also trained technicians. To this end, the application device may also include a control mechanism for dispensing precise amounts of the adhesive to the desired location. One challenge presented with low viscosity and flowing materials, such as a melted adhesive, is that the material tends to continue flowing and resist clean termination, even when the material is no longer being actively dispensed from its container. This may be observed as "threads" or "strings" of adhesive that may stretch between a dispensed amount of the adhesive and its container. Because this may be undesirable in a surgical setting, the control mechanism may allow for precise manipulation of the adhesive.

It should be understood that the above embodiments, and other embodiments described herein, are provided for explanatory purposes, and are not intended to be limiting.

II. EXAMPLE SYSTEMS

An example system 100, shown in FIG. 1, may include a fixation device 110 and an adhesive 120. The fixation device 110 may be any implantable device suitable for being affixed to a bone surface for the repair or joining of one or more bone segments. Using the adhesive 120, the fixation device 110 may be affixed to a bone surface without, the use of screws or other fixation implements requiring drilling or physically penetrating into the bone. In some embodiments, the fixation device 110 may be a plate 130 having at least one face 132 for being affixed to a bone surface. As will be described in more detail below, plate 130 may be provided in a number of shapes, sizes and materials and may include one or more surface structures or treatments. The plates 130 can be used in a variety of applications, such as in craniomaxillofacial procedures for the fixation and stabilization of segments of bone off the craniomaxillofacial skeleton during reconstructive surgery. In another embodiment, the bone plates 130 may be used in treating hand fractures or in conjunction with osteotomies.

Various biocompatible adhesives 120 can be used to affix the fixation device 110 to a bone surface. The adhesive 120 may be selected to provide a sufficient mechanical bond either between two bone segments, or between a fixation device 110 and a bone surface. Where the adhesive 120 is used to affix a fixation device 110 to a bone surface, the adhesive must provide sufficient, resistance to the fixation device 110 pulling, away from the hone surface. Further, as the system 100 is used in a surgical setting to repair bone defects, the adhesive 120 may be selected to cure in a moist environment. In some cases, however, the bond provided by the adhesive 120 may need to be broken. The mechanical bond properties of the adhesive 120 must be balanced against the potential need for repositioning a bone plate 130 once it has been affixed to a bone surface. As such, an adhesive 120 may be formulated to be removable, such as with a Freer or Obwegeser elevator, if the position of the plate 130 is not desirable.

The adhesive 120 is bioabsorbable so that the fixation device 110 and adhesive 120 need not be removed from the body. The adhesive 120 should maintain its mechanical bond and not absorb before the bone segments have had sufficient time to join. For example, the adhesive may absorb within 6 to 8 weeks. Alternatively, the adhesive may take up to 1.5 to 2.5 years to absorb. The selected adhesive may be customized to fit the requirements and characteristics of the particular application. In some cases, the absorbability of the adhesive may be selected to match the bioabsorability of the plate, as will be described further below.

Heat-meltable adhesives 120 may also be used. As shown in FIG. 1, the adhesive 120 may initially be in a solid state and may, in some embodiments, be melted in and dispensed from an application device 140 onto the fixation device 110 or bone surface. In surgical settings, temperatures up, to 2000° C. are regularly used in hemostasis or electrocaudory procedures. Accordingly, the heat-meltable adhesive may have a melting point up to 2000° C. In other examples, the adhesive may have a melting point between 60 and 90° C. The adhesive 120 may also be selected to have a melting point at or below 60° C.

Specific examples of adhesives 120 for use in the system 100 may include heat-meltable polymers, such as poly-DL-lactide (PDLLA), Poly(lactic acid) (PLA) and polyester-based polymers. Polymer blends, such as PLA and a polyester (e.g., poly(ethylene/butylene succinate)) may also be used. In particular, the adhesive 120 may comprise a polymer blend, such as the polymer blend(s) described in patent application U.S. patent application Ser. No. 11/787,076 entitled: Novel Biodegradable Bone Plates And Bonding Systems, which is hereby incorporated by reference in its entirety. The adhesive 120 may comprise a combination of one or more of the above.

The system 100 may also include an application device 140 for dispensing the adhesive 120 onto one or more of a bone surface and the fixation device 110. Adhesive 120, in either a solid or flowable form, may be introduced into the application device 140 via an opening 142 to an internal chamber (not shown), which may be sealed with a closure 144. A user may hold the application device 140 by a grip portion 148 and advance adhesive within the chamber towards a nozzle 146 via trigger 150. In some examples, solid adhesive 120 may be melted inside of the chamber and dispensed from the application device 140. Accordingly, the application device may include an electrical connection 152. Further details of the application device will be discussed below.

III. EXAMPLE PLATES

Figure 2:
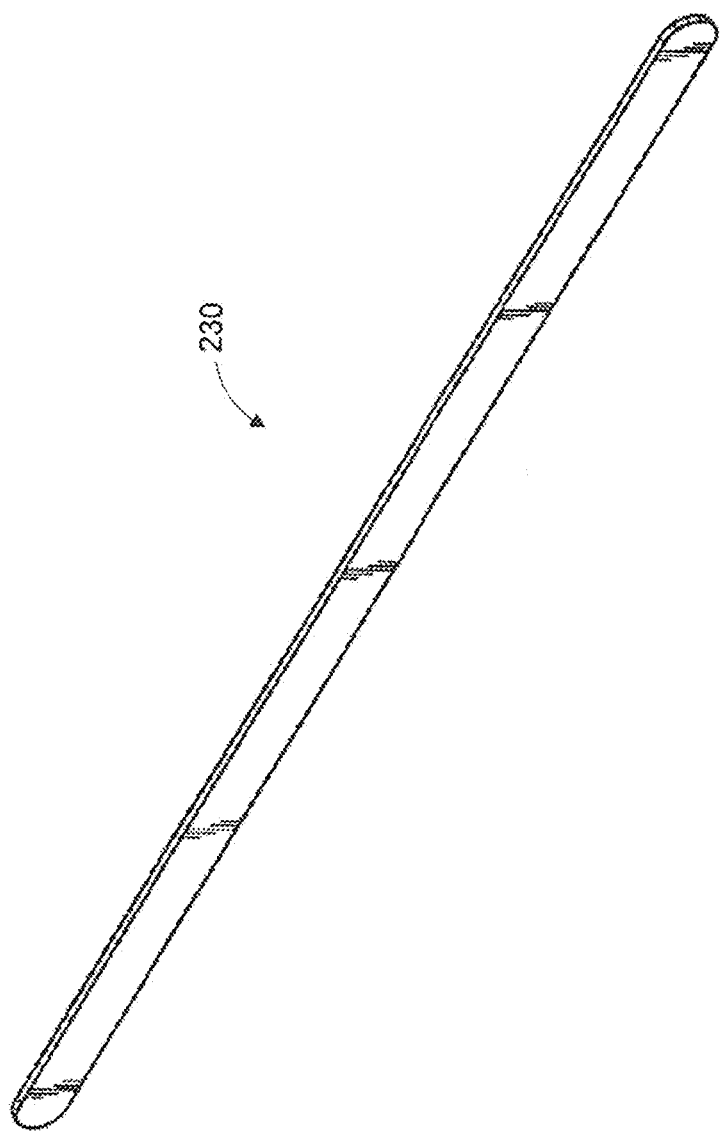
FIG. 2 illustrates an example plate for use in the system of FIG.
Figure 3:
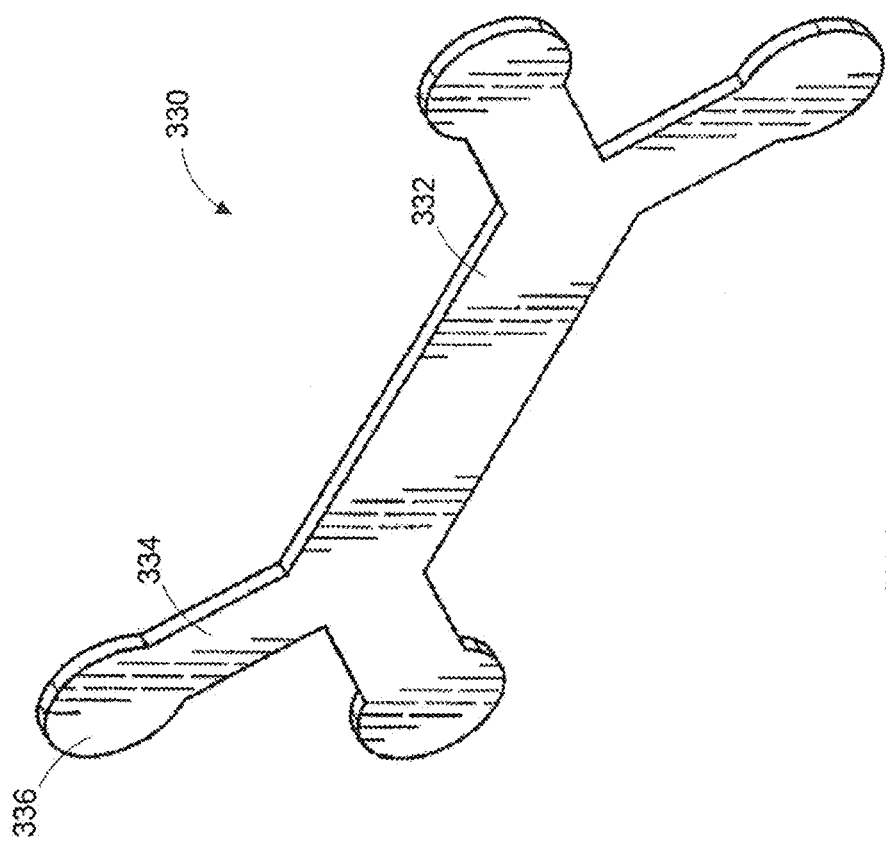
FIG. 3 illustrates an example plate for use in the system of FIG. 1.
Figure 4:
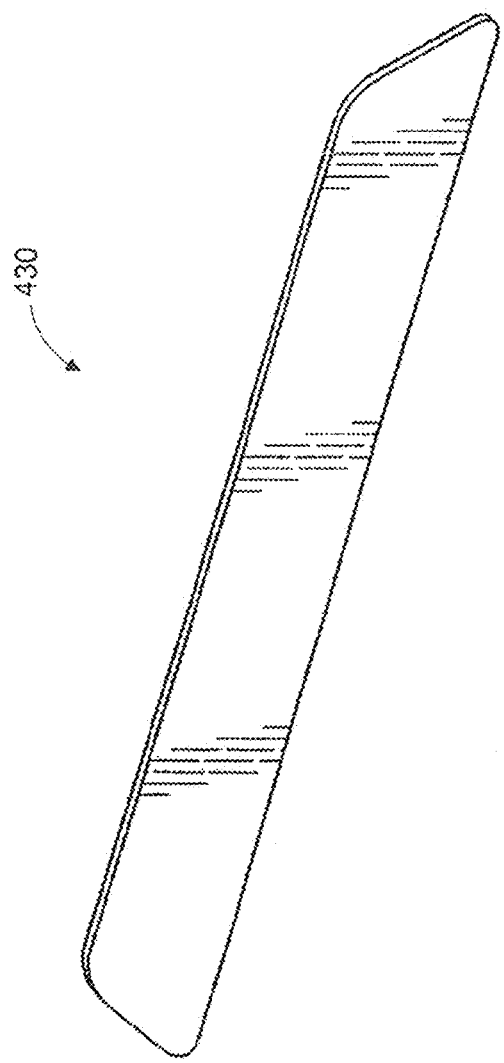
FIG. 4 illustrates an example plate for use in the system of FIG. 1.
Figure 5:
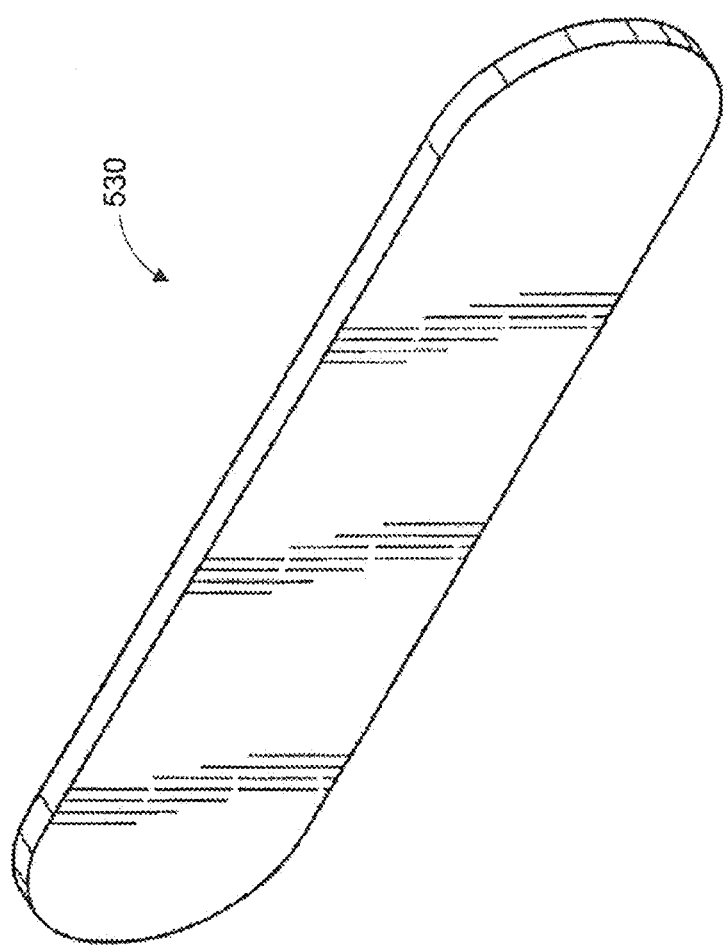
FIG. 5 illustrates an example plate for use in the system of FIG. 1.
Figure 6:
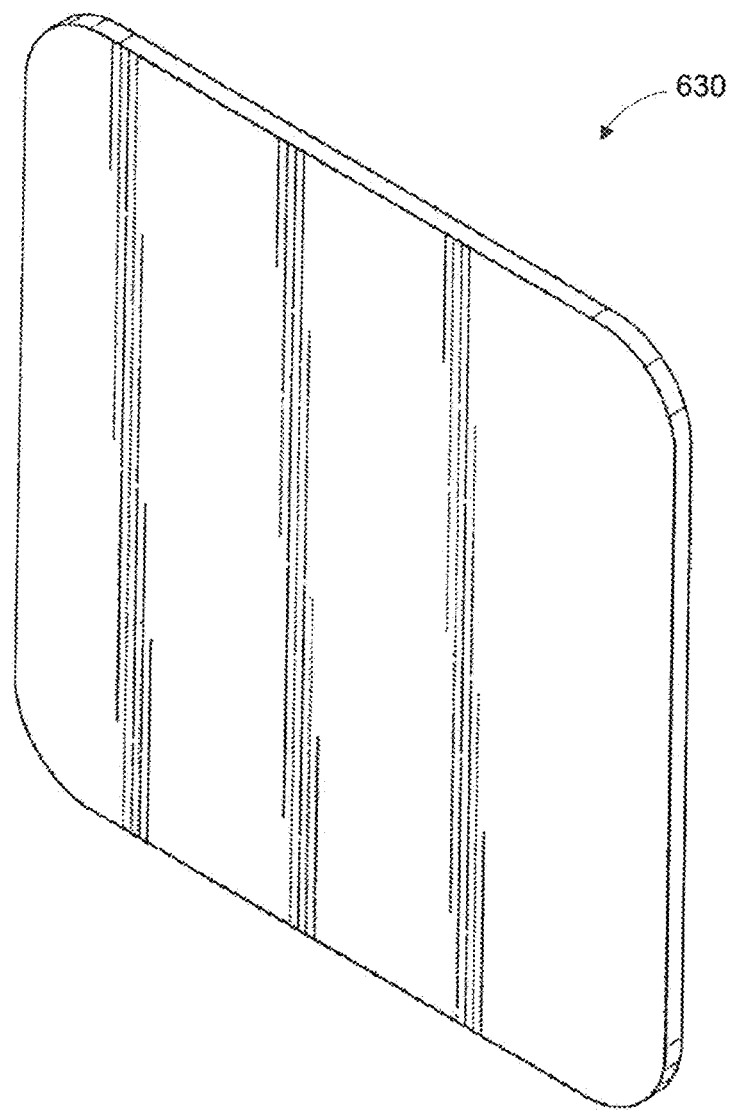
FIG. 6 illustrates an example plate for use in the system of FIG. 1.
Figure 7:
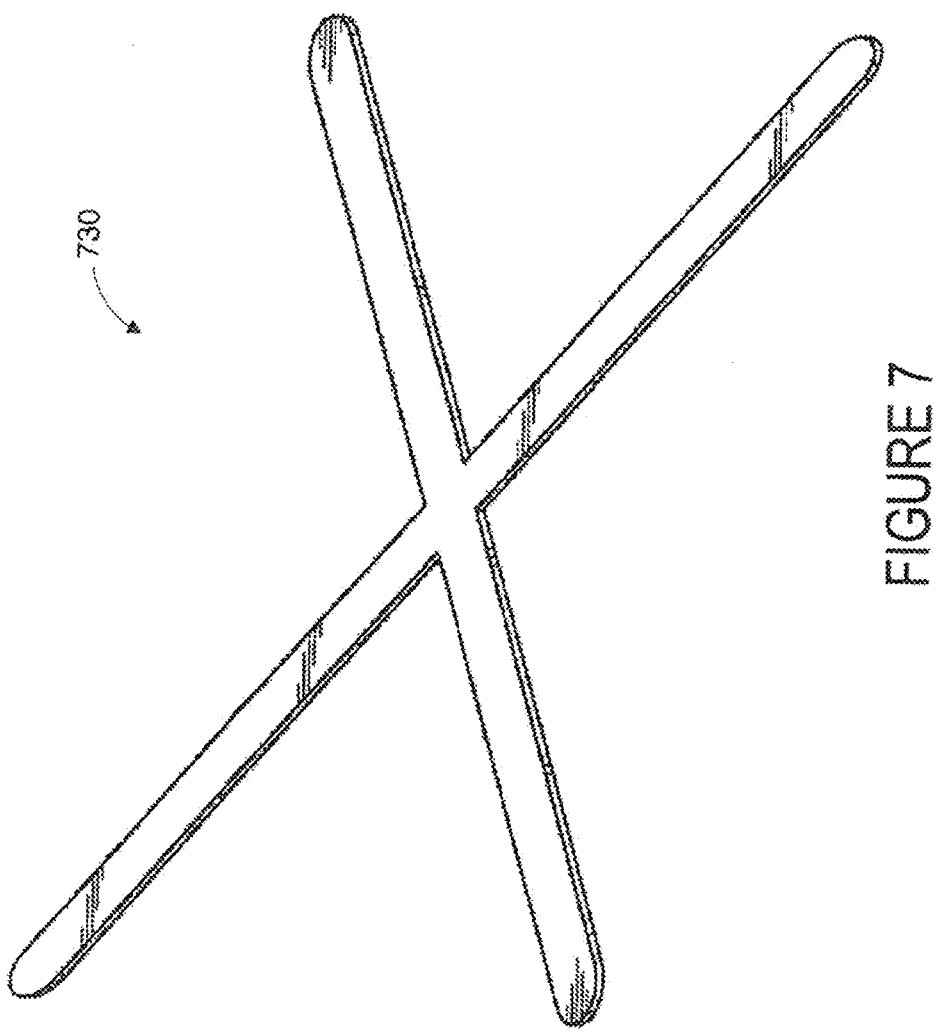
FIG. 7 illustrates an example plate for use in the system of FIG. 1.
Figure 8:
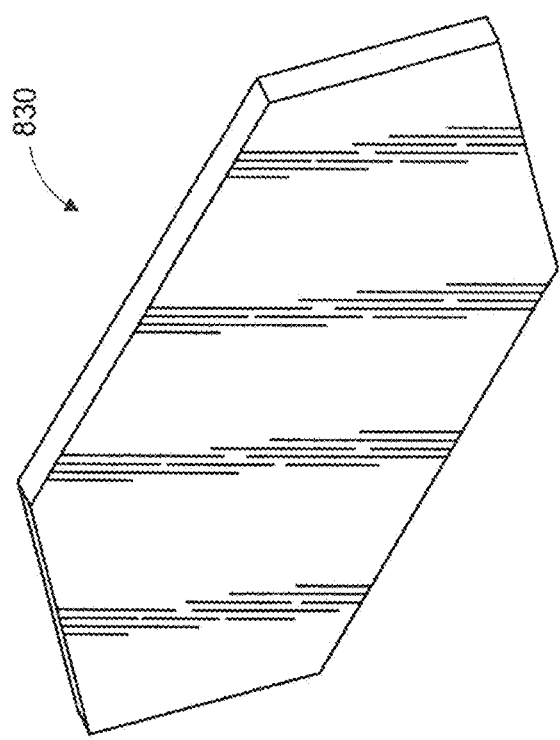
FIG. 8 illustrates an example plate for use in the system of FIG. 1.

Various example plates 130-1130 are shown in FIGS. 1-11. The plates 130 may be fabricated in a number of sizes and shapes from which a surgeon may select according to the type and parameters of the repair and needs of the patient. FIG. 1 shows a bone plate having a generally arcuate shape. FIG. 2 shows a bone plate 230 in the shape of an elongate rod. FIG. 3 shows another example bone plate 330 having an elongated body 332 with one or more members 334 extending from the ends of the body. The members 334 may terminate in pads 336 for receiving adhesive 120. FIG. 4 shows a bone plate 430 that is generally rectangular in shape. The ends of the plate 430 may be fabricated or cut at various angles, depending on the requirements of the surgical procedure. FIG. 5 shows a plate 530 in the shape of an elongate disk. FIG. 6 shows a bone plate 630 that is generally square in shape. FIG. 7 depicts a bone plate 730 that is cross-shaped. Various polygonal shapes may also be used, for example, the hexagon-shaped bone plate 830 shown in FIG. 8. Many other shapes, such as "T," "Y" and "L" shaped plates are also contemplated. The plates can also be fabricated in a number of thicknesses. In some examples, the plate may be between 1 and 1.5 mm thick.

It is also contemplated that bone plates may be cut to size and shape from a substrate, material to suit the needs of the particular patient, area of placement, and procedure. In some examples, the substrate may be fabricated in larger sheets or as a tape that can be cut to size and tailored to the preferences of the surgeon, the type of surgery being performed, the characteristics of the bone or bones being repaired, and the patient, etc. For example, the length, width and, overall shape of the plate may be selected or adjusted to match or be appropriate for the length and size of a particular bone defect or to bridge a gap between bone segments.

The plate material may be chosen to have different strengths, flexibilities, biodegradation and chemical, release properties, all of which may be chosen or customized based on a particular need and application. The material and mechanical properties of the plate material may be chosen based on the size, shape, location and type of bone defect and the age, weight and level of activity of the patient. For example, a patient with a low level of mobility (such, as an infant or older adult) or a bone defect in a low-stress or movement area of the body may not require a fastener with very high tensile strength. Similarly, a large or deep bone defect may demand a plate of larger size or higher strength than a small or superficial defect. Areas of the body in which the bones are under high strain may require a plate material of a larger size or higher strength than bones that are under lower strain.

For some repairs and locations, it may be desirable to bend the plate to fit the curvature of the bone surface. As will be readily appreciated by those of skill in the art, the integrity of a bone repair using the plate and adhesive system described herein may be maximized by tailoring shape of the plate to follow the shape of the bone being repaired. For example, the plate may be bent to match the curvature of a patient's skull, bones. Accordingly, a flexible material may also be selected for the plate. Further, the requisite flexibility or malleability of some materials may also be achieved by heating the plate, for example, between 40 to 60° C.

The plate may be fabricated from various biocompatible materials, in some examples, bioabsorbable plastics such as poly-DL-lactide (PDLLA), polylactate, polyglycolide, polydioxane, polycaprolactone, or other related classes of polymers may be used. Absorbable biocompatible materials may have the benefit of not requiring removal from the body, which often requires an additional surgical procedure. In some applications, a plate which is more or less quickly biodegraded may be selected. The plates may be fabricated from a blend of bioabsorbable polymer materials, such as blends of polylactic acid (PLA)-based polymers or copolymers and polymers or co-polymers of polyesters. The types and amounts of polymers used in the blend can be selected to tailor the bioabsorbability and other properties of the plate.

Figure 9:
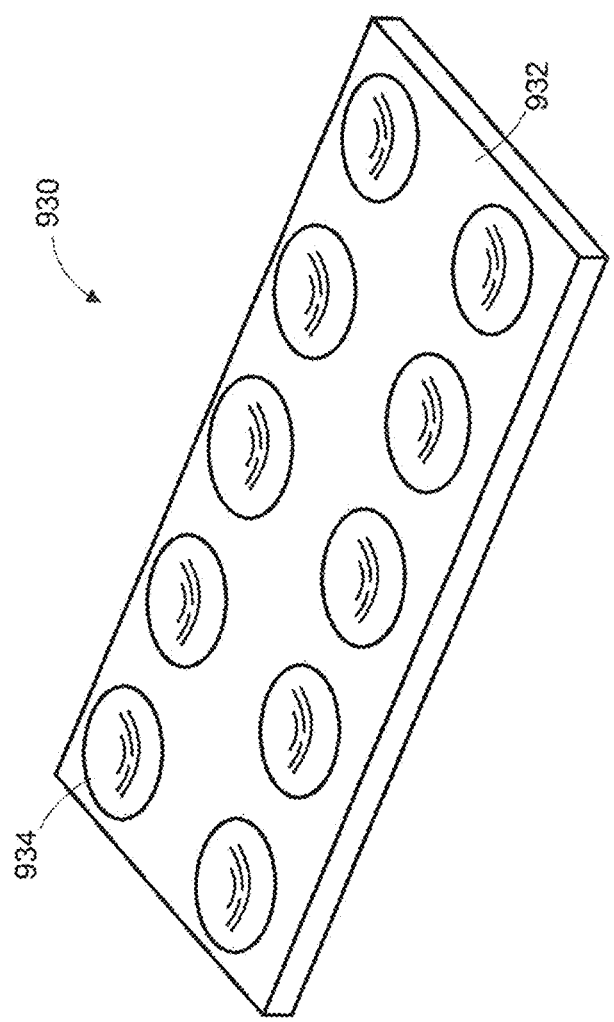
FIG. 9 illustrates an example plate for use in the system of FIG. 1.
Figure 10:
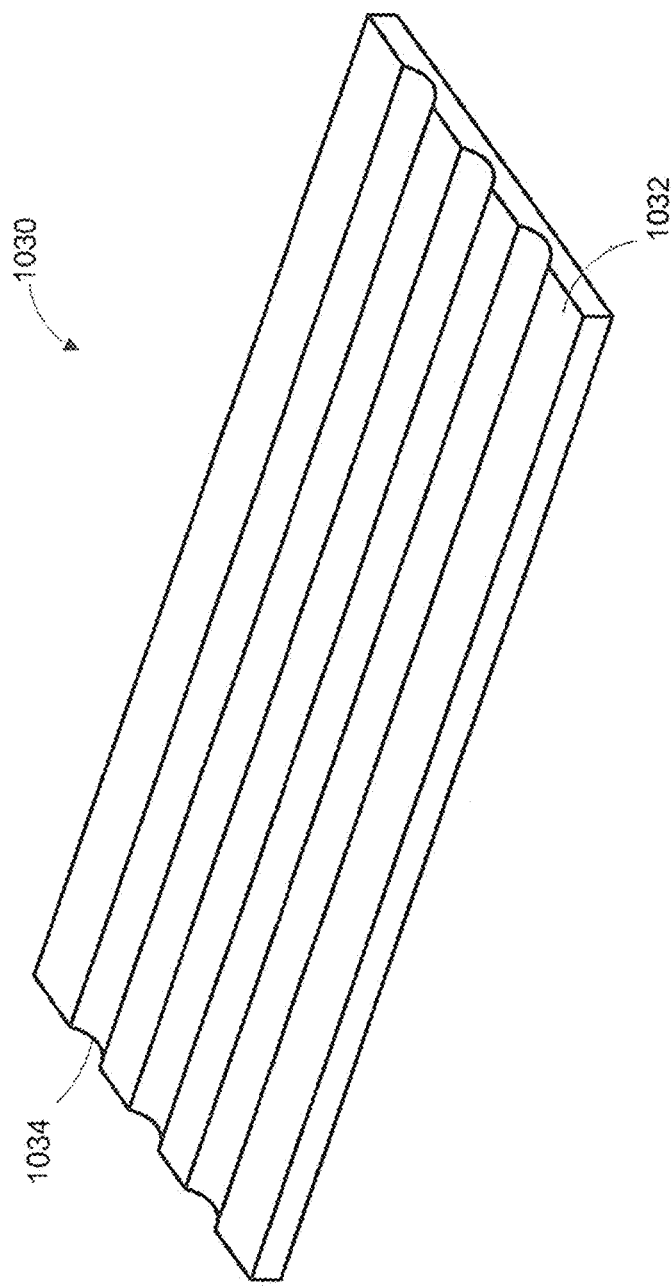
FIG. 10 illustrates an example plate for use in the system of FIG. 1.

As shown in FIGS. 9 and 10, the plates 930, 1030 may also be provided with one or more indentations 934, 1034. For example, the plate 930 may have a face 932, configured to be affixed to a bone surface, having a plurality of dimples 934 disposed thereon. FIG. 10 illustrates plurality of grooves 1034 disposed, on a face 1032 of the plate 1030. The dimples 934 and grooves 1034 arc designed to receive an amount of the adhesive therein. Both the dimples 934 and grooves 1034 provide a convenient guide for loading the plates with the adhesive, not only with respect to where the adhesive should optimally be placed, but also with respect to the amount of adhesive that should be applied. Moreover, the indentations 934, 1034 may provide for a more robust mechanical bond between a plate and a bone surface. When dispensed, adhesive will aggregate into the indentations and a meniscus of adhesive will extend beyond the surface of the plate.

The depth of the indentations may be up to approximately 50% of the depth of the plate. For example, where the plate is 1.5 mm thick, the indentations may be between 0.5 and 0.75 mm deep. The indentations may also be provided in various numbers, arrangements, densities, aspect ratios and patterns on the face of the plate. For example, as shown in FIG. 9, the dimples 934 may be arranged in one or more rows and columns. The dimples 934 in these one or more rows and columns may be aligned, as shown in FIG. 9. Alternatively, the dimples 934 may be provided in a staggered pattern on a face 932 of the plate 930. In some cases, staggering the dimples 934 may lend mechanical stability to the bond between the plate and the bone surface. The dimples 934 may be formed in many sizes and may be arranged at various sparing. In one example, the dimples 934 may be approximately 3 mm in diameter and may be spaced, approximately 3 mm apart. Further, as shown in FIG. 10, the grooves 1034 may be oriented along the length of the plate 1030. Alternatively, the grooves 1034 may be oriented along the width of the plate 1030. Other types, numbers and arrangements of indentations are also contemplated.

In some examples, the plate may also be porous, for example, a mesh. The size of the pores (e.g., openings in the mesh) may be such that wound healing and bone repair is minimally impacted and, in some cases, facilitated. Oxygenation may be used to create pores in the plate material. Pore sizes may be chosen to allow adjacent tissue ingrowth to penetrate through the substrate on one side of the wound, attach to cells on the other side of the wound, and repair the site. In some examples, pores may range in size from 50 (am to 1 mm. Use of a porous material may permit more rapid resorption of the plates. Traditional bioabsorbable materials take between 1.5 to 2.5 years to degrade. However, as bone healing occurs fully between 6 and 8 weeks following a bone fixation procedure, fixation systems are not required beyond this time point. Plate porosity may permit controlled plate resorption within 3-6 months following placement, considerably earlier than other resorbable plating systems. The bioabsorption properties of the plate also be controlled based on the thickness of the plate. Generally, the thinner the plate, the more rapidly it will resorb.

Further, the plate may also include, be coated with, impregnated with or be infused with medicinal agents, such as drugs or other substances that may be released as the plate material biodegrades. For example, the medicinal agents may include substances for promoting wound healing, such as growth factors, substances for decreasing blood viscosity, substances for reducing platelet aggregation, anti-inflammatories, analgesics, substances for promoting blood clotting or antiseptic, antimicrobial or antibacterial substances. More specifically, the medicinal agent(s) may include vitamin A, a steroid and an antibiotic. In embodiments where the plate is porous or includes a porous portion, the pores be impregnated with biologically-active (bioactive) molecules. The size of the pores, and hence the degree of porosity, can be selectively controlled to permit medicinal agents of varying sizes to be impregnated into the structure of the plates. The medicinal agents) may also be encapsulated in hollow microparticles, such as microspheres and nanospheres, which are then loaded unto or onto the plates for time-release delivery of the agent(s).

Figure 11:
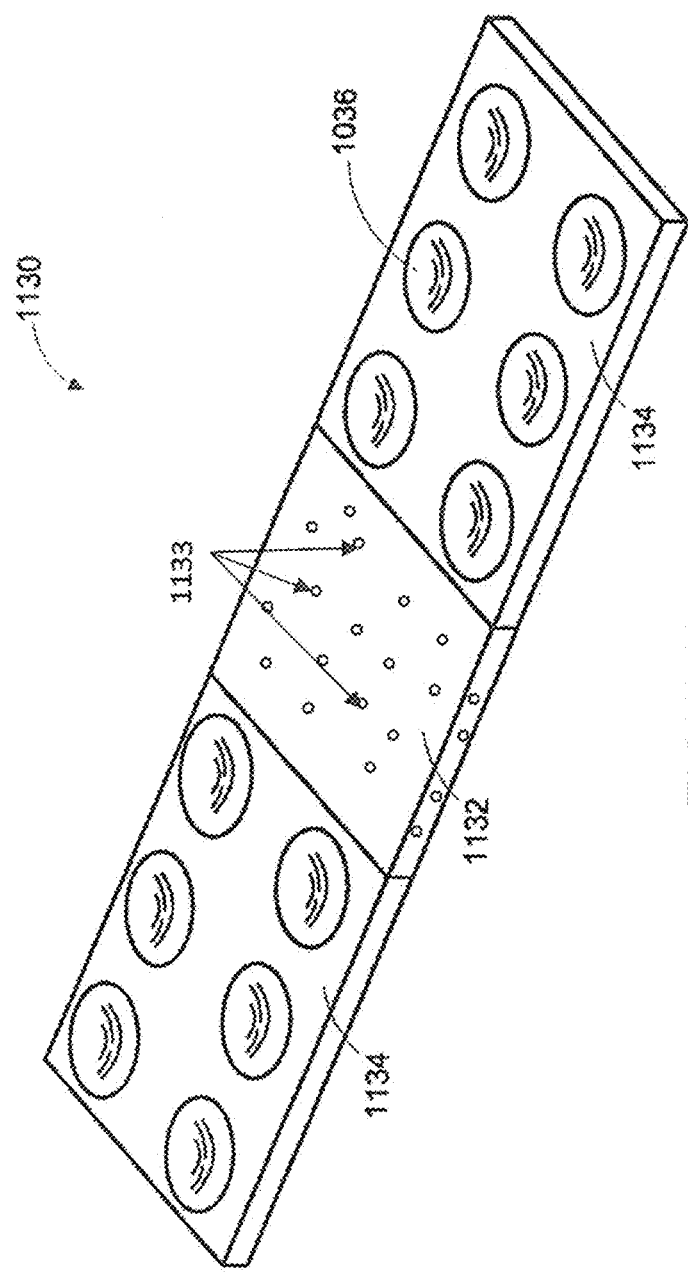
FIG. 11 illustrates an example plate for use in the system of FIG. 1.

As shown in FIG. 11, a plate 1130 may also be provided with a bioactive portion 1132 and one or more adhesive portions 1134. In operation, the bioactive portion 1132, which may be impregnated with a medicinal agent, may be placed over a boundary between two adjacent bone segments intended to be joined. In a preferred embodiment, the medicinal agent(s) arc encapsulated in microparticles, such as nanospheres (shown schematically as 1133), which are embedded within the porous bioactive portion 1132. The one or more adhesive portions 1134 may be loaded with adhesive, such as in one or more dimples 1136, and affixed to the two adjacent bone segments on either side of the boundary. In this configuration, the adhesive will not interfere with the action of the medicinal agent on the bioactive segment. The porous bioactive portion is illustrated in FIG. 11 just by way of example. It should be understood that a porous bioactive portion may be incorporated into any number of bone plate configurations, including but not limited to those shown in FIGS. 2-7. The porous section 1132 of a biodegradable bone plate 1130 may be formed by using a foaming technique, or comparable technique that introduces consistent pores therein to create a porous construct.

Figure 21:
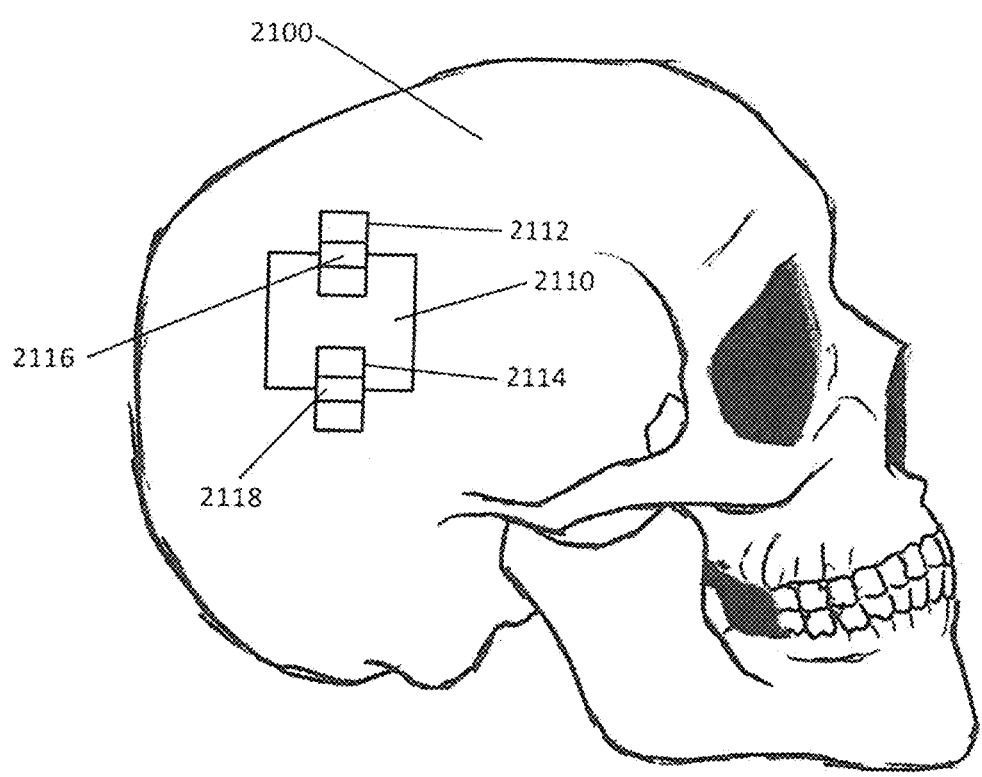
FIG. 21 is a schematic of a preferred use of a preferred embodiment of the bone plate of FIG. 11.

Referring to FIG. 21, a schematic of a partial cranium 2100 upon which an osteotomy was been performed is depicted. After the surgical procedure on the brain is completed, the cut piece of bone 2110 is reinserted into the opening. Bone plates 2112 and 2114 are adhered to and bridge the gap or intersection between the out piece of bone 2110 and the cranium 2100. The porous bioactive portions 2116 and 2118 of bone plates 2112 and 2114, respectively, which include the embedded microcapsules, is positioned over the gap or intersection. The release of the medicinal agents at the desired site aids in bone healing between the cut bone 2110 and the cranium.

The implants of the invention can be manufactured as a unitary whole, as for example, by injection molding or may alternatively be made, as components to be assembled using the bonding system or systems disclosed herein.

The plates can be fabricated using numerous manufacturing routes. For plates having standard sizes and shapes, many conventional processing techniques can be used, including, but not limited to injection molding, compression molding, blow molding, thermoforming, die pressing, slip casting, electrochemical machining, laser cutting, water-jet machining, electrophoretic deposition, powder infection molding, sand casting, shell mold casting, lost foam casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing spinning, and powder metallurgy compaction.

IV. EXAMPLE APPLICATION DEVICES

An example application device 1200 for dispensing adhesive onto a fixation device, such as a plate, or a bone surface is shown in FIGS. 12 and 13A-13D. Application device 1200 may include a housing 1210 enclosing a body 1220 defining a chamber 1222 therein for containing an adhesive, terminating in a nozzle 1230 from which the adhesive is dispensed. Adhesive may be advanced within the chamber by a piston 1240 slidably disposed within the chamber. A gasket 1242 may also be provided at an end of the piston 1240 for sealing the piston 1230 within the chamber 1222. The application device 1200 may also include a control mechanism 1250 for controlling release of adhesive from the nozzle 1230.

Figure 12:
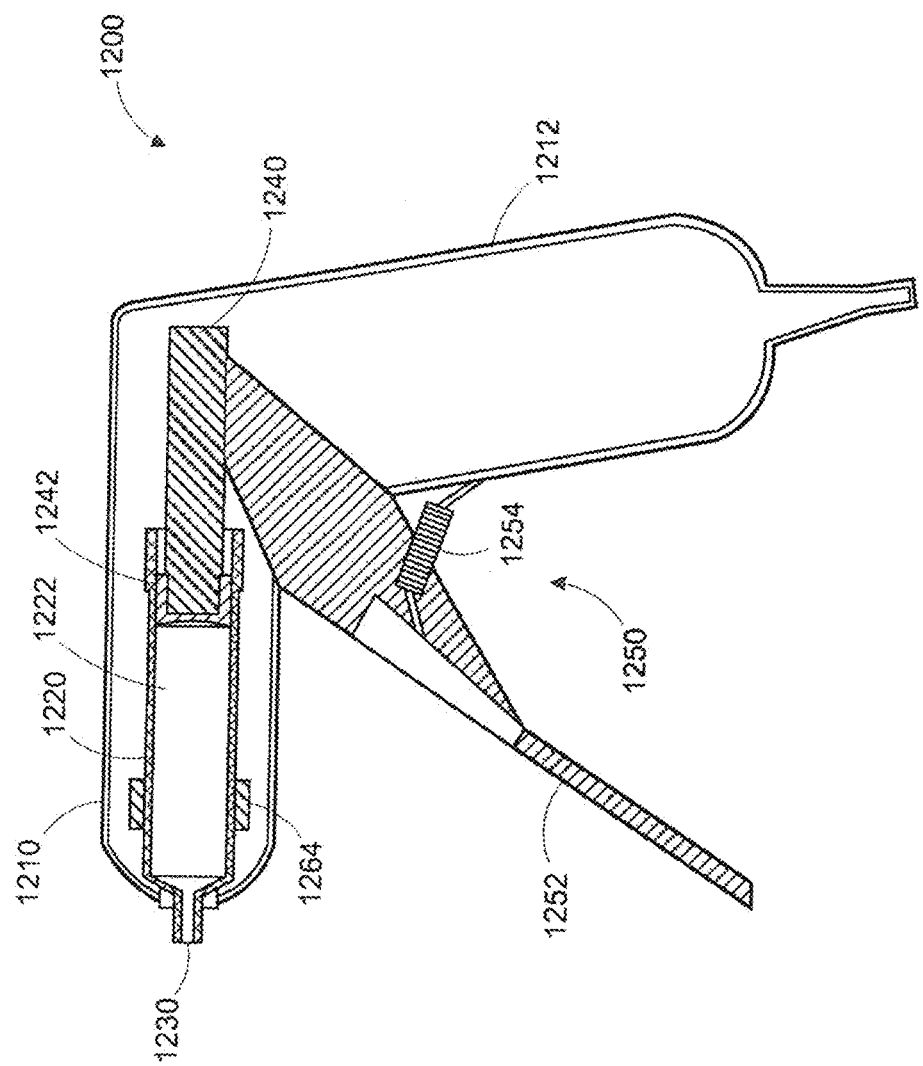
FIG. 12 is a cross-sectional view of an example application device for use in the system of FIG. 1.

In one example, shown in FIG. 12, the control mechanism 1250 may include an actuator 1252, which may be similar to a trigger, having active position and a released position (FIG. 12). The actuator 1252 is in operative communication with the piston 1240 such that depressing the actuator 1252, or moving it from the released position to an active position, causes the piston 1240 to advance within the chamber 1222 towards the nozzle 1230. Because of its levered-orientation, depressing the actuator 1252 towards the housing will cause the piston to be driven towards the nozzle. In operation, a user may manipulate the application device 1200 with a single hand by holding, at a grip portion 1212 and compressing the actuator with his or her lingers to dispense the adhesive. The control mechanism 1250 may also include a spring 1254 for biasing the actuator in a released position, shown in FIG. 12. Releasing the actuator retracts the piston within the chamber away from the nozzle, thereby creating a negative pressure within the chamber. This negative pressure acts on the adhesive within the chamber, causing it to be pulled back away from the nozzle. As such, the control mechanism 1250 allows a user to dispense controlled amounts of adhesive from the application device 1200 and prevents additional adhesive from trailing out of the nozzle after the intended amount has been dispensed. Other embodiments of the control mechanism 1250 are also contemplated. For example, the control mechanism 1250 may also include a blade-like element for physically cutting the string of adhesive or a shutter-like element for closing off the nozzle at a desired point.

Figure 14:
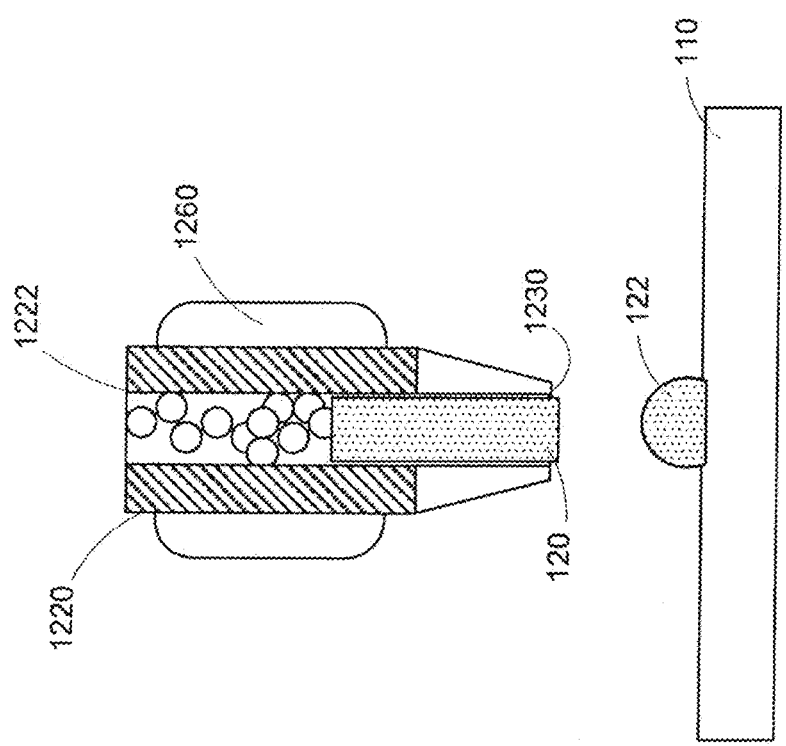
FIG. 14 is a side partial cross-sectional view of a portion of an example application device for use in the system of FIG. 1, shown applying a bead of adhesive to a fixation device.

An adhesive, such as any of those described above, in either a solid or flowable form, may be introduced into the chamber 1222. A solid adhesive may be in the form of pellets, sticks or portions thereof. In some examples, a solid adhesive may be melted or otherwise converted to a flowable form inside of the chamber, as shown in FIG. 14. Accordingly, the application device 1200 may also include one or more heating elements 1260 in communication with the chamber 1222. The heating element(s) 1260 may be any type of device capable of melting the solid adhesive within the chamber. As used herein, the term "melting" means raising the temperature of a solid adhesive to its melting point or a temperature at which it will flow. As with some of the adhesives described above, the heating element(s) may be capable of heating the adhesive within the chamber 1222 up to at least 60° C. and in some cases between 60° C., and 69° C. In some examples, the heating element(s) 1260 may be ceramic or resistive heaters. One or more heater housings 1262 may be coupled to the body 1220 via clamp 1264 for holding the one or more heating elements 1260, as shown in FIG. 13C. Accordingly, the body 1220 may be made of a heat-conducting material.

Figure 15:
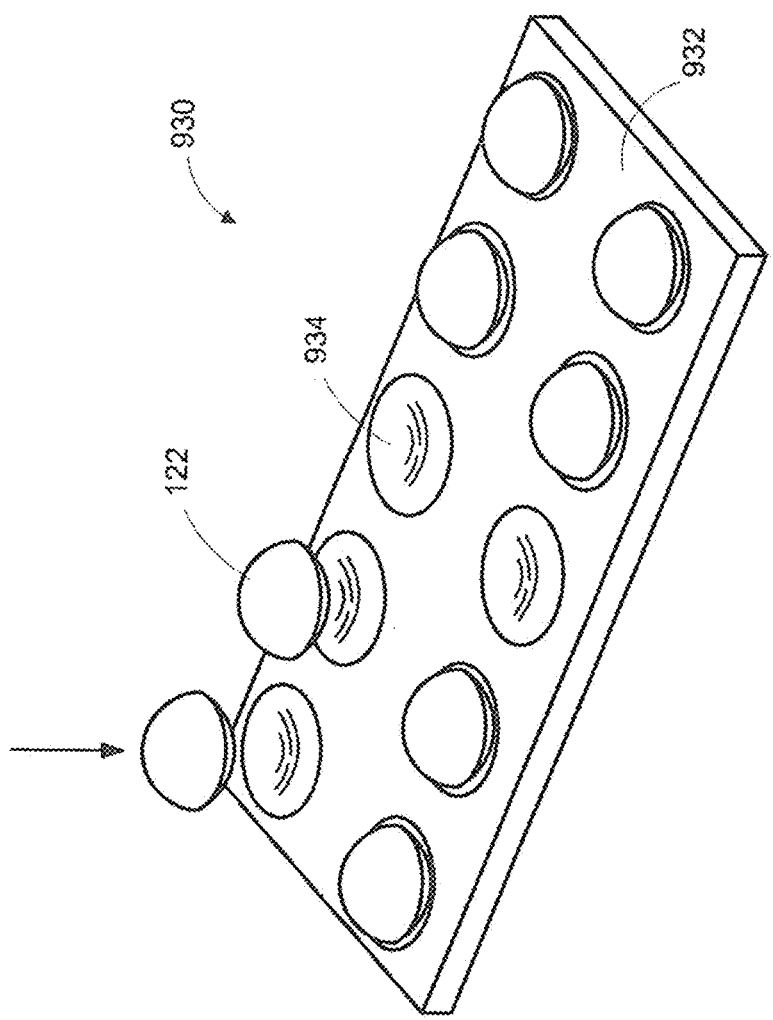
FIG. 15 is a view of an example plate for use in the system of FIG. 1, shown with beads of adhesive being applied thereto.

As shown in FIGS. 14 and 16A-16B, a solid adhesive 120 is melted in the chamber 1222 by one or more heating elements 1260 and dispensed onto a fixation device 110. The nozzle 1230 may b shaped to dispense a melted adhesive 120 as a bead 122 (FIG. 14) or a ribbon 124 (FIGS. 16A, 16B). Beads 122 of adhesive may be dispensed into the dimples 934 of a dimpled plate, such as plate 930, as shown in FIG. 15. Accordingly, the nozzle 1230 may be shaped to dispense a volume of adhesive 120 that will fit within the dimple and, in some cases, create a meniscus above the plate surface 932. To create a ribbon 124 of adhesive, the nozzle 1230 may have a more narrow opening, as shown in FIG. 16A, which may depart a more thin and flat shape to the dispensed adhesive. In some examples, the application device 1200 may be provided with a fixed nozzle shape, such that different application devices are used to create either a bead 122 or ribbon 124 of adhesive. In other examples, a single application device 1200 may have a set of interchangeable nozzles for creating either a bead or ribbon, or various sizes and shapes of beads or ribbons, are provided and may be changed out depending on the particular application. Alternatively, the application device 1200 may be provided with a dual-shaped nozzle that can be toggled or flipped between a bead-dispensing nozzle and a ribbon-dispensing nozzle.

In other examples, heating and melting of the adhesive can be accomplished without an application device. Heating of the adhesive can be done, pre-operatively to form an assembly, can be done outside the body but in the operating room to customize implants at the time of surgery, or can be done during surgery, in the body when the bond is needed within the human body. Any suitable heat generating apparatus can be used to heat and soften or spot weld the adhesive material, such as a laser, a hot air gun, a small welding or soldering gun, or a Bovie

V. ILLUSTRATIVE METHODS

Figure 17:
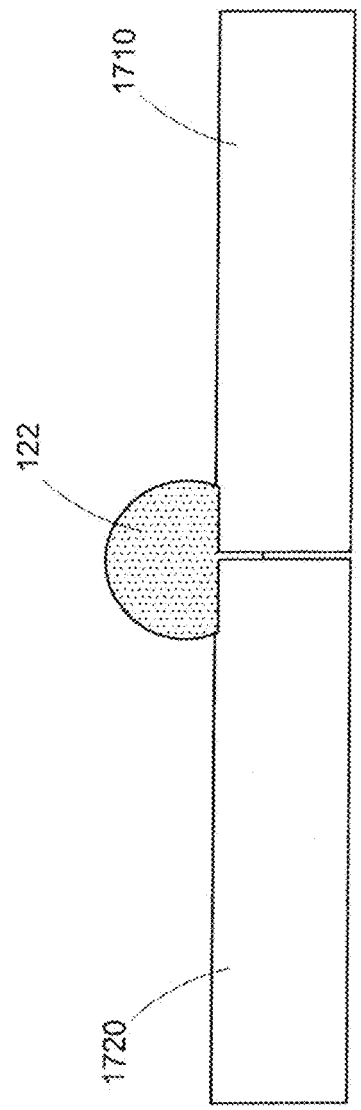
FIG. 17 illustrates an example method for joining bone segments.
Figure 18:
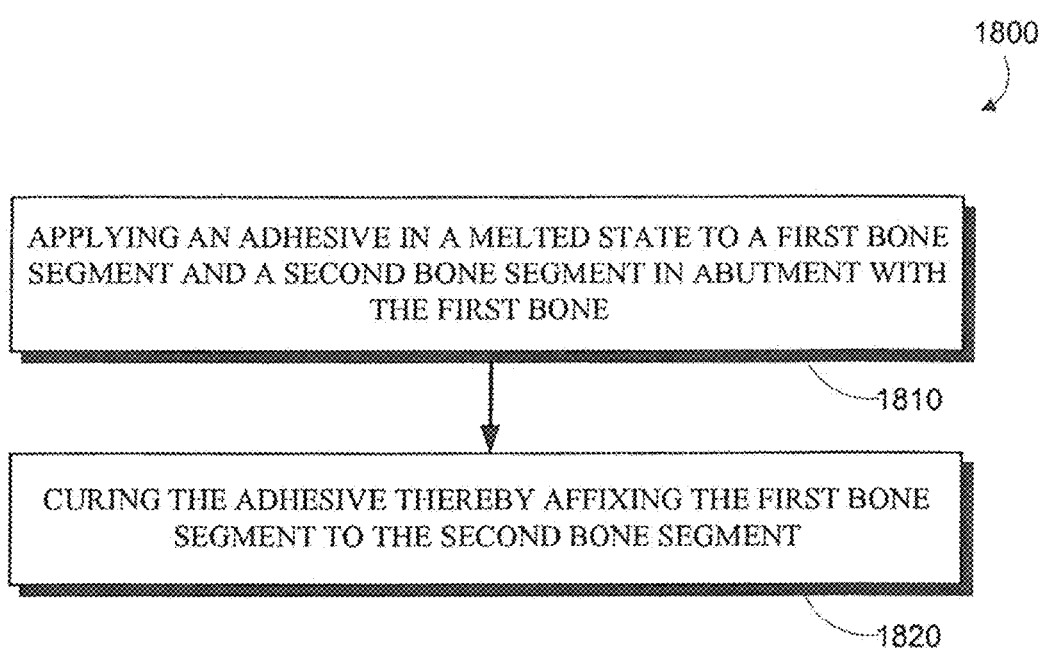
FIG. 18 is a flowchart of an example method.

At least, two fixation methods are contemplated herein. In a first example method, illustrated in FIG. 17, adhesive 120 is applied directly to a site of interest, such as a bone fracture or osteotomy, without the use of another fixation means such as a plate, pin or screw. Accordingly, the adhesive 120 alone is used to affix a first bone segment 1710 to a second bone segment 1720. FIG. 18 is a flowchart of an example method 1800 for affixing at least two bone segments. In a first step, a bead of adhesive 122 is applied in a melted state to a first bone segment and a second bone segment in abutment with the first bone segment (1810). The adhesive is then cured, thereby affixing the first bone segment to the second bone segment (1820). As used herein, the terms "cure" or "cured" should be interpreted in its broadest possible sense to include any means, process or state by which the adhesive is allowed to set or transition from a melted to a solid or semi-solid state, thereby joining the surfaces it contacts. In some cases, the adhesive may be cured over time, without any external assistance. In other examples, heat, pressure or light may be applied to aid in curing of the adhesive. To join the at least two bone segments, at least one bead of adhesive may be applied to the first and second segments. Additional stability may be provided by dispensing a bead of adhesive on Moore than one seam between abutting bone fragments.

This method of joining bone may be useful in a number of situations where plating systems are not feasible. There are a number of advantages in using such a plate-less bonding technique including: the elimination of the need for plates and instrumentation as well as simplification of technique for operating room personnel; the elimination of the need for subsequent plate removal that is often necessary due to the plate's interference with extensor tendon function in the hand or its palpability beneath the scalp; and the reduction of operating room time. For example, the method can be used in place of a plate, pin or screw, such as certain types of hand and craniofacial fractures where bone plates may be contraindicated such as: hand fractures close to the articular surface where there may be inadequate room for placement of a plate; hand fractures close to the ephiphyseal growth plate in children where there is inadequate room for plate placement; non-displaced or minimally displaced hand and craniofacial fractures requiring stabilization, the fractures, being in locations where, placement of plates is not feasible; severely comminuted fractures where stabilization by pure bonding (without plates) is the only option; and hand fractures in the elderly patient in whom plate placement may not be feasible due to confounding medical issues such as inadequate bone stock amenable to other modalities.

Figure 19:
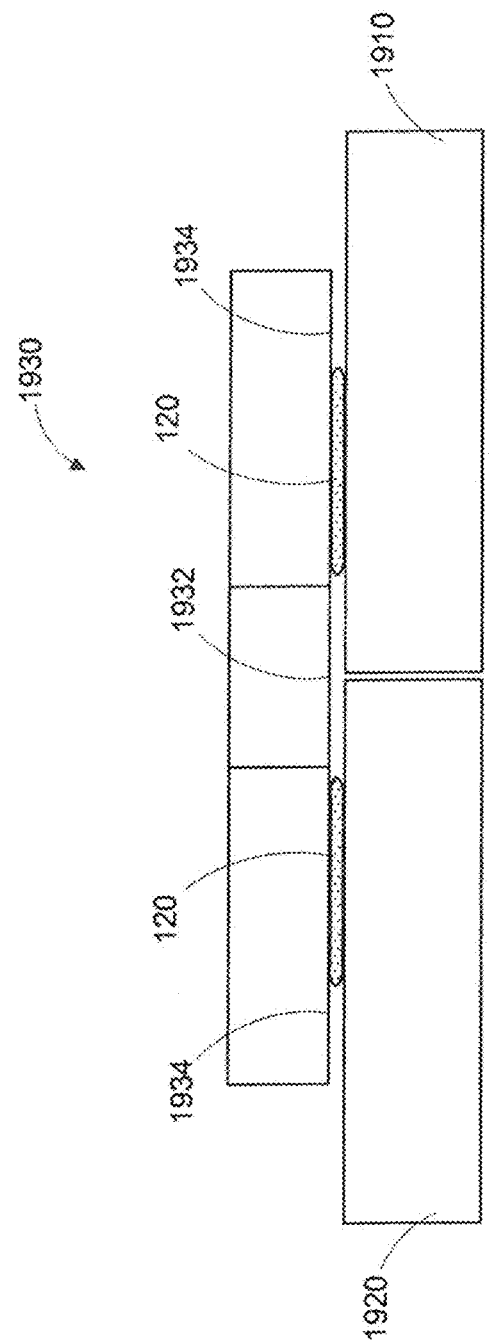
FIG. 19 illustrates an example method for joining bone segments.
Figure 20:
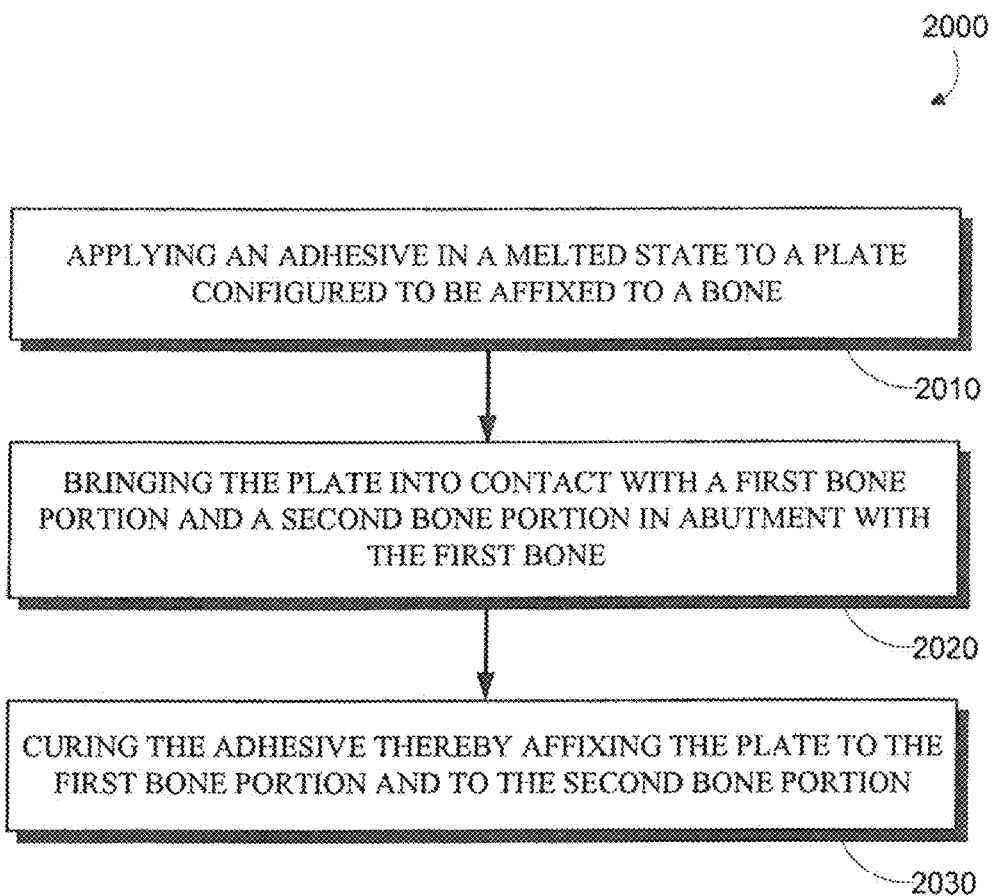
FIG. 20 is a flowchart of an example method.

Another example method is illustrated in FIGS. 19 and 20. In this example method, a plate 1930, which may include any of plates 130-1030, is used to affix a first bone segment 1910 and a second bone segment 1920. A flowchart of an example method 2000 for affixing at least two bone segments with a plate is shown in FIG. 20. In a first step, an adhesive is applied in a melted state to a plate configured to be affixed to a bone (2010). The adhesive may either be directly applied to the plate itself, or may be applied to the surface of a bone where the plate is to be affixed. The plate is brought into contact with a first bone segment and a second bone segment in abutment with the first bone segment (2020) and the adhesive is cured, thereby affixing the plate to the first bone segment and to the second bone segment (2030). In some embodiments, the adhesive is melted and dispensed onto to the plate by an application device, such as devices 140 or 1200 described above.

In some examples, the plate 1930 may include a dimpled portion 1934, having one or more dimples, and a bioactive portion 1932, which may include at least one medicinal agent. The bioactive portion 1932 may be brought into contact with the first bone segment 1910 and the second bone segment 1920 in the area where the second bone segment abuts the first bone segment 1910, such as at a scam 1940. The dimpled portions 1934 are placed on the first 1910 and second bone segments 1920, on either side of the seam 1940.

VI. CONCLUSION

While various aspects and embodiments have been disclosed herein, other aspects and embodiments will be apparent to those skilled in the art. The various aspects and embodiments disclosed wherein are for purposes of illustration and are not intended to be limiting, with the true scope being indicated by the following claims.

I claim:

1. A system comprising:
  a bone plate adapted to be affixed to a bone surface, wherein at least a portion of the bone plate is configured with at least one bioactive portion to incorporate bioactive substances therewith, said at least one bioactive portions being substantially free of adhesive, said bioactive substances including bone healing-promoting substances, the bone plate further comprising at least one attachment portion; and
  an adhesive adapted to be applied to the at least one attachment portion to affix the bone plate to the bone surface.

2. The system of claim 1, the at least one bioactive portion further being porous and the bone healing-promoting substances being embedded therein.

3. The system of claim 2, wherein the at least one bioactive portion comprises a plurality of hollow microparticles encapsulating the bone healing-promoting substances.

4. The system of claim 1, the at least one attachment portion further comprising at least one face defining at least one indentation and configured to retain an amount of adhesive.

5. The system of claim 1, the at least one bioactive portion being porous and further comprising a plurality of microspheres, the micro spheres containing the bone healing promoting substances, and the at least one attachment portion further comprising at least one face defining at least one indentation and configured to retain an amount of adhesive.

6. The system of claim 1, wherein the bone plate and the adhesive comprises an unblended polymer material.

7. The system of claim 6, wherein the unblended polymer comprises a poly lactic acid (PLA) or a PLA-based polymer.

\* \* \* \* \*